US010006094B2

(12) United States Patent
Huang et al.

(10) Patent No.: US 10,006,094 B2
(45) Date of Patent: Jun. 26, 2018

(54) **METHODS FOR DISCRIMINATING INTERSPECIFIC RELATIONSHIPS AND INTRASPECIFIC RELATIONSHIPS OF LACTIC ACID BACTERIA OF *LACTOBACILLUS CASEI* GROUP BY USING MUTL OR DNAJ DEGENERATE PRIMERS**

(71) Applicant: FOOD INDUSTRY RESEARCH AND DEVELOPMENT INSTITUTE, Hsinchu (TW)

(72) Inventors: Chien-Hsun Huang, Chiayi County (TW); Li-Na Huang, Hsinchu County (TW); Li-Ting Wang, Hsinchu (TW)

(73) Assignee: Food Industry Research And Development Institute, Hsinchu (TW)

( * ) Notice: Subject to any disclaimer, the term of this patent is extended or adjusted under 35 U.S.C. 154(b) by 360 days.

(21) Appl. No.: 14/959,587

(22) Filed: Dec. 4, 2015

(65) Prior Publication Data

US 2017/0058327 A1 Mar. 2, 2017

(30) Foreign Application Priority Data

Aug. 28, 2015 (TW) .............................. 104128512 A (51) Int. Cl.
 *C12P 19/34* (2006.01)
 *C12Q 1/689* (2018.01)
(52) U.S. Cl.
 CPC ....... *C12Q 1/689* (2013.01); *C12Q 2600/172* (2013.01)
(58) Field of Classification Search
 None
 See application file for complete search history.

(56) References Cited

U.S. PATENT DOCUMENTS 7,402,411 B2 * 7/2008 Chang .................... C12Q 1/701
 435/5

FOREIGN PATENT DOCUMENTS

WO WO2013/100810 A2 7/2013

OTHER PUBLICATIONS

Office action and search report dated Apr. 18, 2017 for the corresponding Japaneses application 2015-237794.
English translation of the office action dated Apr. 18, 2017 for the corresponding Japaneses application 2015-237794.
Huang, Chien-Hsun & Lee, Fwu-Ling, "The dnaK gene as a molecular marker for th3e classification and discrimination of Labobacillus casei group," Antonie van Leeuwenhoek, 2011, vol. 99, pp. 319-327.
Cai, Hui et al., "Genotypic and phenotypic characterization of Lactobacillus casei strains isolated from different ecological niches suggests frequent recombination and niche specificity," Microbiology, 2007, vol. 153, pp. 2655-2665.
Iacumin, Lucilla et al., "High resoluiton melting anslysis (HRM) as a new tool for the identification of species belonging to the *Lactobacillus casei* group and comparison with species-specific PCRs and multiplex PCR," Food Microbiology, Sep. 9, 2014, vol. 46, pp. 357-367.
Huang, Chien-Hsun et al., "Simultaneous discrimination of species and strains in *Lactobacillus rhamnosus* using species-specific PCR combined with multiplex mini-sequencing technology," Molecular and Cellular Probes, Jun. 30, 2015, vol. 29, pp. 531-533.
Itoh, Yoko et al., "dnaJ and gyrB gene sequence relationship among species and strains of genus *Streptococcus*," Systematic and Applied Microbiology, 2006, vol. 29, pp. 368-374.
Zhang, Jiwei et al., "DnaJ sequences of Bacillus cereus strains isolated from outbreaks of hospital infection and are highly simlar to Bacillus anthracis," Diagnostic Microbiology and Infectious Disease, 2011, vol. 70, pp. 307-315.
Shah, Mohammad Monir et al., "dnaJ gene sequence-based assay for species identification and phylogenetic grouping in the genus *Staphylococcus*," International Journal of Systematic and Evolutionary Microbiology, 2007, vol. 57, pp. 25-30.
Morita Yukio et al., "Genetic diversity of the dnaJ gene in the *Mycobacterium avium* complex," Journal of Medical Microbiology, 2004, vol. 53, pp. 813-817.
Nhung, Pham Hong et al., "The dnaJ gene as a novel phylogenetic marker for identificatioin of *Vibrio* species," Systematic and Applied Mcrobiology, 2007, vol. 30, pp. 309-315.
Diancourt et al., "Multilocus Sequence Typing of Lactobacillus casei Reveals a Clonal Population Structure with Low Levels of Homologeous Recombination," Applied and Environmental Microbiology, 2007, vol. 73, pp. 6601-6611.
Office action and search report dated Jun. 21, 2016 for the corresponding Taiwan application 104128512.
English translation of the search report dated Jun. 21, 2016 for the corresponding Taiwan application 104128512.
Cai, H., et al., "Genotypic and phenotypic characterization of Lactobacillus casei strains isolated from different ecological niches suggests frequent recombination and niche specificity," Microbiology, 2007, vol. 153, p. 2655-2665.
GenBank: ABJ70979.1 (2006).
Laure Diancourt et al., "Multilocus Sequence Typing of Latobacillus casei Reveals a Clonal Population Structure with Low Levels of Homologous Recombination." Applied and Environmental Microbiology, Oct. 2007, pp. 6601-6611.
Hui Cai et al., "Genotypic and Phenotypic Characterization of Lactobacillus casei Strains Isolated from Different Ecological Niches Suggests Frequent Recombination and Niche Specificity." Microbiology, 153, pp. 2655-2665, 2007.
Stephen F. Altschul et al., "Basic Local Alignment Search Tool." J. Mol. Biol. 215:403-410, 1990.
James J Campanella et al., "MatGAT: An application that generates similarity/identity matrices using protein or DNA sequences." BMC Bioinformatics, 4:29, 2003.

(Continued)

*Primary Examiner* — Kenneth R Horlick
(74) *Attorney, Agent, or Firm* — WPAT, P.C., Intellectual Property Attorneys; Anthony King (57) ABSTRACT

Degenerate primers for amplifying fragments of the nucleotide sequences of mutL and dnaJ genes of a lactic acid bacterium of *Lactobacillus casei* group are provided. Methods and kits for discriminating interspecies and intraspecies of a lactic acid bacteria of *Lb. casei* group are also provided.

16 Claims, 2 Drawing Sheets

(56) References Cited

OTHER PUBLICATIONS

P. Librado and J. Rozas, "DnaSP v5: a software for comprehensive analysis of DNA polymorphism data." Bioinformatic, 25:1451-1452, 2009.
Naruya Saitou and Masatoshi Nei, "The neighbor-joining method: a new method for reconstructing phylogenetic trees." Mol Biol Evol;1987; 4:406-425.
Julie D. Thompson et al., "The CLUSTAL_X windows interface: flexible strategies for multiple sequence alignment aided by quality analysis tools." Nucleic AcidsRes 25:4876-4882, 1997.
Julie D. Thompson et al., "CLUSTAL W: improving the sensitivity of progressive multiple sequence alignment through sequence weighting, position-specific gap penalties and weight matrix choice." Nucleic Acids Research 22: 4673-4680,1994.

* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Lactobacillus sp.

<400> SEQUENCE: 1
attgaycarc tatckgcmac                                               20

<210> SEQ ID NO 2
<211> LENGTH: 19
<212> TYPE: DNA
<213> ORGANISM: Lactobacillus sp.

<400> SEQUENCE: 2
gagccrtaac cggcaatma                                                19

<210> SEQ ID NO 3
<211> LENGTH: 21
<212> TYPE: DNA
<213> ORGANISM: Lactobacillus sp.

<400> SEQUENCE: 3
tctgaayttv gtytgrcttt g                                             21

<210> SEQ ID NO 4
<211> LENGTH: 18
<212> TYPE: DNA
<213> ORGANISM: Lactobacillus sp.

<400> SEQUENCE: 4
gtggtgcvca rgckaatc                                                 18
```

METHODS FOR DISCRIMINATING INTERSPECIFIC RELATIONSHIPS AND INTRASPECIFIC RELATIONSHIPS OF LACTIC ACID BACTERIA OF *LACTOBACILLUS CASEI* GROUP BY USING MUTL OR DNAJ DEGENERATE PRIMERS

FIELD OF THE APPLICATION

The present application relates to a method for identifying the related taxa of lactic acid bacteria of *Lactobacillus casei* group by using a primer pair to amplify the sequence of a specific targeted gene, and then sequencing and comparing the amplified sequence.

BACKGROUND

The species of *Lactobacillus casei* group, including *Lb. casei*, *Lb. paracasei* and *Lb. rhamnosus*, are generally recognized as safe (GRAS), and are widely used for commercial probiotics or as microorganisms for producing yogurt products. However, these species are taxonomically closely related. The genotypes and phenotypes of the species are very similar (the average similarity of the 16S rRNA genes among the species is >98.9%), so it is difficult to correctly distinguish species from each other. Furthermore, the functional characteristics of each probiotic are strain specific. Therefore, the Food and Agriculture Organization (FAO) and World Health Organization (WHO) of the United Nations announced in 2002 that it is essential to identify the scientific name of a probiotic to the strain level.

Pulsed-field gel electrophoresis (PFGE) is commonly used as the gold standard method for species discrimination and differentiation of different microorganisms. Although said method can achieve the purpose of intraspecies discrimination, it is complex and time-consuming. The reproducibility of the method is still a problem.

Multilocus sequence typing (MLST) is a more recent, highly developed taxonomic technique. Basically, MLST is established by sequencing 6-7 housekeeping genes having about 450 bp, and then aligning the sequences of these housekeeping genes to identify the mutated bases among the sequences so as to determine the sequence type (ST) of a microorganism. Since MLST provides good discrimination and reproducibility, and since it can be used to establish sequence information databanks and compare the sequences from different laboratories, MLST can not only improve the accuracy of PFGE but also replace it.

Cai et al. ("Genotypic and Phenotypic Characterization of *Lactobacillus casei* Strains Isolated from Different Ecological Niches Suggests Frequent Recombination and Niche Specificity." Microbiology, 153, pp. 2655-2665, 2007) and Diancourt et al. ("Multilocus Sequence Typing of *Lactobacillus casei* Reveals a Clonal Population Structure with Low Levels of Homologous Recombination." Applied and Environmental Microbiology, October 2007, pp. 6601-6611) used MLST to classify 40 and 52 strains of *Lb. casei* to 36 and 31 haplotypes, respectively. These and other publications have identified and selected many protein encoding genes, such as recA, yycH, dnaK, hsp60, tuf rpoA and pheS (preferably, recA, yycH, and pheS), as the markers for classifying *Lb. casei*. However, most of these identifying markers can only classify the microorganism to the species level, but cannot effectively determine different strains among the same species. In addition, MLST requires comparing and sequencing 6 to 7 gene loci so as to discriminate the bacterium. Therefore, MLST is also time-consuming and costly.

Alekseeva et al. (WO2013/100810 A2) used sequence alignment to compare the sequences of the fragments of MazEF and RelBE gene of the edible lactic acid bacteria, including *Lb. acidophilus*, *Lb. helveticus*, *Lb. plantarum*, *Lb. paracasei*, and *Lb. rhamnosus* to identify the inter- and intraspecies discriminations of the bacteria. The results of Alekseeva et al. show that the sequence similarity of the MazEF gene of *Lb. paracasei* and *Lb. rhamnosus* is about 83%, and thus these two bacteria can be distinguished from each other based on the gene. However, Alekseeva et al. did not include in the comparison the bacterium *Lb. casei*, which is closely related in taxonomy to those species. In addition, Alekseeva et al. did not use *Lb. rhamnosus* as a type strain for comparison. Therefore, the results of Alekseeva et al. cannot determine whether MazEF gene can be used to distinguish the interspecies relationship among *Lb. casei*, *Lb. paracasei* and *Lb. rhamnosus*. In the intraspecies discrimination, Alekseeva et al. found that through the MazEF gene analyses, 7 strains of *Lb. paracasei* can be classified into 3 haplotypes; and through the relE1 gene analyses, 5 strains of *Lb. rhamnosus* can be classified into 3 haplotypes.

Therefore, in this technical field, there is still a need to develop a method which can easily, quickly, simultaneously, and accurately identify the inter- and intraspecies relationships of the lactic acid bacteria.

SUMMARY OF THE INVENTION

One aspect of the invention provides a degenerate primer pair, which is capable of amplifying a partial fragment of the nucleotide sequence of mutL (DNA mismatch repair protein) gene or a partial fragment of the nucleotide sequence of dnaJ (heat shock protein) gene.

Another aspect of the invention provides a composition comprising one or more degenerate primers, which can be used to amplify a partial fragment of the nucleotide sequence of mutL gene or a partial fragment of the nucleotide sequence of dnaJ gene.

Another aspect of the invention provides a method for determining the species of a lactic acid bacterium of *Lb. casei* group by using the above mentioned primer pair or composition.

Another aspect of the invention provides a method for determining whether or not a lactic acid bacterium of *Lb. casei* group and the other two or more lactic acid bacteria that are of the same species but different strains are of the same haplotype.

Another aspect of the invention provides a kit comprising the above mentioned primer pair or composition.

The present invention is described in detail in the following sections. Other characterizations, purposes and advantages of the present invention can be easily found in the detailed descriptions and claims of the invention.

DETAILED DESCRIPTION

The present invention can be understood more readily by reference to the following detailed description of various embodiments of the invention, the examples, and the tables with their relevant descriptions. Unless otherwise defined, all terms (including technical and scientific terms) used herein have the same meaning as commonly understood by one of ordinary skill in the art to which this invention belongs. It will be further understood that terms such as those defined in commonly used dictionaries should be interpreted consistently with their meaning in the context of the relevant art and will not be interpreted in an idealized or overly formal sense unless expressly so defined herein. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±20%, preferably ±10%, and even more preferably ±5%.

As used therein, the term "isolated" or "isolation" means that the material is removed from its original environment (e.g., the natural environment if it is naturally existing). The term "isolated" or "isolation" does not necessarily reflect the extent to which the material has been purified.

As used herein, the term "percent identity" or "percent identical" means the identical level of the same loci on the two or more sequences after comparing and aligning two or more polynucleotide sequences; and the term "percent similarity" or "percent similar" means the identical level of the bases of the two or more sequences after comparing and aligning two or more polynucleotide sequences.

As used herein, a "type strain" represents a model strain, which can be used as a reference to compare with another strain to determine whether the two stains are of the same species.

As used herein, the term "primer" represents an oligonucleotide having about 15 to 45 nucleic acid bases, which is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. The term "degenerate primer" means that one or more codes of the primer are substituted with a degenerate code.

As used herein, the term "haplotype" refers to a combination pattern of single nucleotide polymorphisms (SNPs) found on the amplified sequences.

One purpose of the present invention is to provide primer pairs, which can be used to amplify the partial fragments of mutL and dnaJ genes of lactic acid bacteria, respectively. In a preferred embodiment of the present invention, the primer pairs are degenerate primer pairs.

As described herein, in the primer pair which can be used to amplify a partial fragment of the nucleotide sequence of mutL gene, first primer mixture comprises the nucleotide sequences shown as 5'-ATTGAYCARCTATCKGCMAC-3' (SEQ ID NO: 1), wherein Y=C or T; R=A or G; K=G or T; and M=A or C, and the second primer mixture comprises the nucleotide sequences shown as 5'-GAGCCRTAACCG-GCAATMA-3' (SEQ ID NO: 2), wherein R=A or G; and M=A or C.

As described herein, in the primer pair which can be used to amplify a partial fragment of the nucleotide sequence of dnaJ gene, the first primer mixture comprises the nucleotide sequences shown as 5'-TCTGAAYTTVGTYTGRCTTTG-3' (SEQ ID NO: 3), wherein Y=C or T; V=G, A or C; and R=A or G, and the second primer mixture comprises the nucleotide sequences shown as f 5'-GTGGTGCVCARGC-KAATC-3' (SEQ ID NO: 4), wherein V=G, A or C; R=A or G; and K=G or T.

The primers of the present invention can be obtained by any method known in the art, such as chemical synthesis method.

Another purpose of the present invention is to provide a composition for amplifying a partial fragment of the nucleotide sequence of mutL gene, which comprises a first primer mixture and/or a second primer mixture, and a solvent, wherein the first primer mixture comprises the nucleotide sequences shown as 5'-ATTGAYCARCTATCKGCMAC-3' (SEQ ID NO: 1), wherein Y=C or T; R=A or G; K=G or T; and M=A or C, and the second primer mixture comprises the nucleotide sequences shown as 5'-GAGCCRTAACCG-GCAATMA-3' (SEQ ID NO: 2), wherein R=A or G; and M=A or C.

Another purpose of the present invention is to provide a composition for amplifying a partial fragment of the nucleotide sequence of dnaJ gene, which comprises a first primer mixture and/or a second primer mixture, and a solvent, wherein the first primer mixture comprises the nucleotide sequences shown as 5'-TCTGAAYTTVGTYTGRCTTTG-3' (SEQ ID NO: 3), wherein Y=C or T; V=G, A or C; and R=A or G, and the second primer mixture comprises the nucleotide sequences shown as 5'-GTGGTGCVCARGCK-AATC-3' (SEQ ID NO: 4), wherein V=G, A or C; R=A or G; and K=G or T.

In an embodiment of the present invention, the primer mixture contained in the composition is the first primer mixture. In another embodiment of the present invention, the primer mixture contained in the composition is the second primer mixture. In a further embodiment of the present invention, the primer mixture contained in the composition includes the first primer mixture and the second primer mixture.

The solvent contained in the composition of the present invention can be any liquid that can dissolve an oligonucleotide. For example, the solvent can be, but is not limited to, water or a phosphate buffer.

Another purpose of the present invention is to provide a method for determining the species of a lactic acid bacterium of *Lb. casei* group, which comprises:

(a) extracting a DNA sample from the lactic acid bacterium;

(b) using the primer pair or composition disclosed herein to amplify the DNA sample to obtain a partial fragment of the nucleotide sequence of mutL gene and/or a partial fragment of the nucleotide sequence of dnaJ gene;

(c) determining the sequence of the amplified partial fragment; and (d) comparing the determined sequence with the corresponding gene sequences of two or more type strains of *Lb. casei* group to obtain a percent similarity and/or identity to each of the type strains, thereby identifying the lactic acid bacterium as the same species as the type strain of *Lb. casei* group to which the lactic acid bacterium has the highest percent similarity and/or identity.

As used herein, the term "a lactic acid bacterium of *Lb. casei* group" means that the lactic acid bacterium has been determined to one species of the *Lb. casei* group.

In step (a) of the present invention, the method for extracting the DNA sample from the lactic acid bacterium can be any method known in the art. DNeasy Blood & Tissue Kit (Qiagen, U.S.A.) and FavorPrep Blood/Cultured Cell Genomic DNA Extraction Mini Kit (Favorgen Biotech, Taiwan) may be used as non-limiting examples for extracting and purifying the sample.

In step (b) of the present invention, "amplify" represents any methods that can be used to reproduce a polynucleotide sequence so as to obtain many more copies of the polynucleotide molecule. The methods include, but are not limited to, reverse transcription, polymerase chain reaction, and ligase chain reaction.

In an embodiment of the present invention, step (b) uses a first primer mixture/composition and a second primer mixture/composition to amplify the DNA sample to obtain the partial fragment of the nucleotide sequence of mutL gene, wherein the first primer mixture/composition comprises the nucleotide sequences shown as 5'-ATTGAY-CARCTATCKGCMAC-3' (SEQ ID NO: 1), wherein Y=C or T; R=A or G; K=G or T; and M=A or C, and wherein the second primer mixture/composition comprises the nucleotide sequences shown as 5'-GAGCCRTAACCG-GCAATMA-3' (SEQ ID NO: 2), wherein R=A or G; and M=A or C. In another embodiment of the present invention, step (b) uses a first primer mixture/composition and a second primer mixture/composition to amplify the DNA sample to obtain the partial fragment of the nucleotide sequence of dnaJ gene, wherein the first primer mixture/composition comprises the nucleotide sequences shown as 5'-TCT-GAAYTTVGTYTGRCTTTG-3' (SEQ ID NO: 3), wherein Y=C or T; V=G, A or C; and R=A or G, and wherein the second primer mixture/composition comprises the nucleotide sequences shown as 5'-GTGGTGCVCARGCKAATC-3' (SEQ ID NO: 4), wherein V=G, A or C; R=A or G; and K=G or T. In a further embodiment of the present invention, the fragments of the nucleotide sequences of both the mutL gene and dnaJ gene are amplified.

In step (c) of the present invention, the type strains of *Lb. casei* group used include, but are not limited to, *Lb. casei* BCRC 10697$^T$ (ATCC 393), *Lb. paracasei* BCRC 12248$^T$ (ATCC 25302) and *Lb. rhamnosus* BCRC BCRC 10940$^T$ (ATCC 12116).

The sequence of a polynucleotide molecule can be determined by any conventional techniques or methods, such as using BigDye Terminator v3.1 Cycle Sequencing Kit (Applied Biosystems, CA, USA) or PRISM 3730 Sequencer (Applied Biosystems).

In step (d) of the present invention, the percent similarity/identity can be measured by using one of the following sequence comparison algorithms or by visual inspection.

For sequence comparison, typically one sequence acts as a reference sequence, to which test sequences are compared. When using a sequence comparison algorithm, test and reference sequences are input into a computer. The sequence comparison algorithm then calculates the percent sequence similarity/identity for the test sequence relative to the reference sequence, based on the designated program parameters.

Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Natl. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of a useful algorithm is PILEUP. PILEUP creates a multiple sequence alignment from a group of related sequences using progressive, pairwise alignments to show relationship and percent sequence similarity/identity. It also plots a phylogenetic tree which can be used to create the alignment. Phylogenetic trees can also be generated by using neighbor-joining (NJ) method (Saitou and Nei, Mol Biol Evol, 4:406-425, 1987). PILEUP uses a simplification of the progressive alignment method of Feng & Doolittle, J. Mol. Evol. 35:351-360, 1987. The method used is similar to the method described by Higgins & Sharp, CABIOS 5:151-153, 1989. Other algorithms that are useful for generating multiple alignments of sequences are Clustal W (Thompson et al., Nucleic Acids Research 22: 4673-4680, 1994) and Clustal X (1.83) (Thompson et al., Nucleic Acids Res 25:4876-4882, 1997).

Another example of an algorithm that is suitable for determining percent sequence identity and sequence similarity is the BLAST algorithm, which is described in Altschul et al., J. Mol. Biol. 215:403-410, 1990. Software for performing BLAST analysis is publicly available through the National Center for Biotechnology Information. MatGAT 2.02 (Campanella et al., BMC Bioinformatics, 4:29, 2003) and Vector NTI v 9.0 (Invitrogen, San Diego, Calif., USA) can also be used to calculate sequence identity/similarity.

After obtaining the sequence identity/similarity of the lactic acid bacterium to each of the type strains of *Lb. casei* group, the lactic acid bacterium is identified as the same species as the type strain of *Lb. casei* group to which the lactic acid bacterium has the highest similarity and/or identity.

Another purpose of the present invention is to provide a method for determining whether a lactic acid bacterium of *Lb. casei* group and the other two or more lactic acid bacteria of *Lb. casei* group that are of the same species but different strains are of the same haplotype or not, which comprises:

(a) extracting a DNA sample from the lactic acid bacterium;

(b) using the primer pair or composition disclosed herein to amplify the DNA sample to obtain a partial fragment of the nucleotide sequence of mutL gene and/or a partial fragment of the nucleotide sequence of dnaJ gene;

(c) determining the sequence of the amplified sequence fragment; and (d) conducting haplotype analysis to compare the determined sequence with each corresponding gene sequence of the other two or more lactic acid bacteria of the same species but different strains; if the analyzed sequences are different from each other, it represents that the compared lactic acid bacteria are of different haplotypes.

Steps (a), (b) and (c) can be conducted by the methods disclosed above. The haplotype analysis in step (d) can be conducted by using DnaSP v.5.0 software (Librado et al., Bioinformatic, 25:1451-1452, 2009) or BioNumerics software (Applied Maths, U.S.A.).

In an embodiment of the present invention, the two or more lactic acid bacteria of *Lb. casei* group of the same species are different strains of *Lb. paracasei*. Examples of the different strains of *Lb. paracasei* include, but are not limited to, *Lb. paracasei* BCRC 12248$^T$, *Lb. paracasei* BCRC 12188, *Lb. paracasei* BCRC 14001, *Lb. paracasei* BCRC 16100, *Lb. paracasei* BCRC 17001, *Lb. paracasei* BCRC 17005, *Lb. paracasei* BCRC 17475, *Lb. paracasei* BCRC 17483, *Lb. paracasei* BCRC 17484, *Lb. paracasei* BCRC 17488, *Lb. paracasei* BCRC 17489, *Lb. paracasei* BCRC 12193, *Lb. paracasei* BCRC 18853, *Lb. paracasei* BCRC 18854, *Lb. paracasei* BCRC 14023, *Lb. paracasei* BCRC 16094, and *Lb. paracasei* BCRC 17002.

In another embodiment of the present invention, the two or more lactic acid bacteria of *Lb. casei* group of the same species are different strains of *Lb. rhamnosus*. Examples of the different strains of *Lb. rhamnosus* include, but are not limited to, *Lb. rhamnosus* BCRC 10940$^T$, *Lb. rhamnosus* BCRC 14029, *Lb. rhamnosus* BCRC 16000, *Lb. rhamnosus* BCRC 16095, *Lb. rhamnosus* BCRC 17004, *Lb. rhamnosus* BCRC 17490, *Lb. rhamnosus* BCRC 80663, and *Lb. rhamnosus* BCRC 80666.

Another purpose of the present invention is to provide a kit for discriminating the interspecies and/or intraspecies of a lactic acid bacterium of *Lb. casei* group, which comprises the primer pair or composition disclosed above, wherein the first primer mixture/composition and the second primer mixture/composition are contained in one container or separate containers.

In the present invention, the kit may further include the sequence information of at least one lactic acid bacterium of *Lb. casei* group for comparison and/or analysis. Said information is included in a computer readable medium of any type, e.g., a disc or a USB flash drive.

The at least one lactic acid bacterium of *Lb. casei* group can be, but is not limited to, *Lb. casei* BCRC 10697$^T$, *Lb. casei* BCRC 17487, *Lb. casei* BCRC 17942, *Lb. casei* BCRC 80156, *Lb. casei* BCRC 17647, *Lb. paracasei* BCRC 12248$^T$, *Lb. paracasei* BCRC 12188, *Lb. paracasei* BCRC 14001, *Lb. paracasei* BCRC 16100, *Lb. paracasei* BCRC 17001, *Lb. paracasei* BCRC 17005, *Lb. paracasei* BCRC 17475, *Lb. paracasei* BCRC 17483, *Lb. paracasei* BCRC 17484, *Lb. paracasei* BCRC 17488, *Lb. paracasei* BCRC 17489, *Lb. paracasei* BCRC 12193, *Lb. paracasei* BCRC 18853, *Lb. paracasei* BCRC 18854, *Lb. paracasei* BCRC 14023, *Lb. paracasei* BCRC 16094, *Lb. rhamnosus* BCRC 10940T, *Lb. rhamnosus* BCRC 14029, *Lb. rhamnosus* BCRC 16000, *Lb. rhamnosus* BCRC 16095, *Lb. rhamnosus* BCRC 17004, *Lb. rhamnosus* BCRC 17490, *Lb. rhamnosus* BCRC 80663, *Lb. rhamnosus* BCRC 80666, or any combinations thereof.

The kit of the present invention may further include an instruction describing the methods disclosed above so as to achieve the discrimination of the interspecies and/or intraspecies of a lactic acid bacterium of *Lb. casei* group.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

Materials and Methods
Sample Collection
1. Lactic Acid Bacterial Strains

All the reference strains (including the type strains and the isolated strains) were provided by the Bioresources Collection and Research Center (BCRC) of the Industry Research And Development Institute (see Table 1).

TABLE 1

| Bacteria Used | No. |
| --- | --- |
| *Lactobacillus casei* | BCRC 10697$^T$ |
| | (ATCC 393) |
| | BCRC 17487 |
| | BCRC 17942 |
| | BCRC 80156 |
| | BCRC 17647 |
| *Lactobacillus paracasei* | BCRC 12248$^T$ |
| | (ATCC 25302) |
| | BCRC 12188 |
| | BCRC 12193 |
| | BCRC 14001 |
| | BCRC 16100 |
| | BCRC 17001 |
| | BCRC 17005 |
| | BCRC 17475 |
| | BCRC 17482 |
| | BCRC 17483 |
| | BCRC 17484 |
| | BCRC 17488 |
| | BCRC 17489 |
| | BCRC 18853 |
| | BCRC 18854 |
| | BCRC 14023 |
| | BCRC 16094 |
| | BCRC 17002 |
| | Isolated Strain 275 |
| *Lactobacillus rhamnosus* | BCRC 10940$^T$ |
| | (ATCC 12116) |
| | BCRC 16000 |
| | BCRC 16095 |
| | BCRC 17004 |
| | BCRC 17490 |
| | BCRC 14029 |
| | BCRC 80663 |
| | BCRC80666 |

$^T$Said strain is a type strain.

2. Incubation Conditions of the Bacterial Strains

MRS agar (Oxoid, Basingstoke, UK) was used as the standard solid medium, and all the strains were anaerobically incubated at 30° C. After the bacteria were incubated at 30° C. for 48 hours, a small amount of fresh bacterial sample was taken and added to a 1.5-mL eppendorf. The DNA of the cells was extracted and purified by using the DNeasy Blood & Tissue kit (Qiagen, U.S.A.), and then dissolved in a suitable amount of deionized water. A small amount of the DNA solution was taken to determine the DNA quality by electrophoresis on 1% agarose gel. The rest of the solution was stored at −20° C. for further use.

Example 1. Determination of mutL Gene

1. Design of Degenerate Primers

The sequences of mutL genes of *Lb. casei* (AP012544; originally named *Lactobacillus casei* subsp. *casei* ATCC 393), *Lb. paracasei* (CP000423; originally named *Lactobacillus casei* ATCC 334) and *Lb. rhamnosus* ATCC 8530 (CP003094) were downloaded from GenBank. The degenerate primers, Lcagp-mutlF3 (5'-ATTGAYCARCTATCK-GCMAC-3' (SEQ ID NO: 1) and Lcagp-mutlR4 (5'-GAGC- CRTAACCGGCAATMA-3' (SEQ ID NO: 2), wherein Y is C or T; R is A or G; K is G or T; and M is A or C, were designed based on the most conserved region of mutL gene.

2. PCR Amplification of mutL Gene and Nucleotide Sequencing

The partial fragments (about 809 bp) of mutL genes of *Lb. casei*, *Lb. paracasei* and *Lb. rhamnosus* were amplified by PCR using the above degenerate primers. PCR reaction conditions were: 30 cycles of 94° C. for 5 min, 94° C. for 1 min, 60° C. for 1 min, and 72° C. for 5 min, and a final extension step at 72° C. for 7 min. The resulting amplicons were purified by using the QIAquick PCR Purification Kit (Qiagen, U.S.A.), and then sequenced with the BigDye Terminator v3.1 Cycle Sequencing Kit (Applied Biosystems, CA, USA) and PRISM 3730 Sequencer (Applied Biosystems).

3. Interspecific Relationship Analysis

The DNA sequences of all strains were aligned by the Clustal X (1.83) program (Thompson et al., 1997), and the identities among the sequences were calculated by the MatGAT 2.02 software (Campanella et al., 2003). Table 2 shows the identities of all the amplified partial fragments of mutL genes of *Lb. casei*, *Lb. paracasei* and *Lb. rhamnosus*. Neighbor-joining method (Saitou and Nei, "The neighbor-joining method: a new method for reconstructing phylogenetic trees." Mol Biol Evol; 1987; 4:406-425) was used to construct the phylogenetic trees of the lactic acid bacteria. As shown in the phylogenetic trees of FIG. 1, different species are distributed in different clusters.

TABLE 2

| | mutL gene sequence identities (%) | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 | 13 |
| 1. *Lactobacillus casei* BCRC 10697[T] | 100 | 99.9 | 100 | 78.8 | 79 | 79 | 79.1 | 79 | 78.8 | 78.7 | 78.8 | 79.1 |
| 2. *Lactobacillus casei* BCRC 17487 | | 99.9 | 100 | 78.8 | 79 | 79 | 79.1 | 79 | 78.8 | 78.7 | 78.8 | 79.1 |
| 3. *Lactobacillus casei* BCRC 17942[T] | | | 99.9 | 78.7 | 78.8 | 78.8 | 79 | 78.8 | 78.7 | 78.6 | 78.7 | 79 |
| 4. *Lactobacillus casei* BCRC 80156 | | | | 78.8 | 79 | 79 | 79.1 | 79 | 78.8 | 78.7 | 78.8 | 79.1 |
| 5. *Lactobacillus paracasei* BCRC 12248[T] | | | | | 98.9 | 99.3 | 99.5 | 99.9 | 99.5 | 99.6 | 99.6 | 99.5 |
| 6. *Lactobacillus paracasei* BCRC 12193 | | | | | | 99.3 | 99.2 | 99 | 99.2 | 99 | 98.8 | 99.5 |
| 7. *Lactobacillus paracasei* BCRC 17482 | | | | | | | 99.6 | 99.5 | 99.6 | 99.5 | 99.2 | 99.9 |
| 8. *Lactobacillus paracasei* BCRC 16100 | | | | | | | | 99.6 | 99.7 | 99.6 | 99.3 | 99.7 |
| 9. *Lactobacillus paracasei* BCRC 17005 | | | | | | | | | 99.6 | 99.7 | 99.7 | 99.6 |
| 10. *Lactobacillus paracasei* BCRC 18853 | | | | | | | | | | 99.6 | 99.3 | 99.7 |
| 11. *Lactobacillus paracasei* BCRC 18854 | | | | | | | | | | | 99.5 | 99.6 |
| 12. *Lactobacillus paracasei* BCRC 17484 | | | | | | | | | | | | 99.3 |
| 13. *Lactobacillus paracasei* BCRC 17488 | | | | | | | | | | | | |
| 14. *Lactobacillus paracasei* BCRC 17489 | | | | | | | | | | | | |
| 15. *Lactobacillus paracasei* BCRC 14023 | | | | | | | | | | | | |
| 16. *Lactobacillus paracasei* BCRC 16094 | | | | | | | | | | | | |
| 17. *Lactobacillus paracasei* BCRC 17002 | | | | | | | | | | | | |
| 18. *Lactobacillus paracasei* BCRC 17475 | | | | | | | | | | | | |
| 19. *Lactobacillus rhamnosus* BCRC 10940[T] | | | | | | | | | | | | |
| 20. *Lactobacillus rhamnosus* BCRC 16000 | | | | | | | | | | | | |
| 21. *Lactobacillus rhamnosus* BCRC 16095 | | | | | | | | | | | | |
| 22. *Lactobacillus rhamnosus* BCRC 17490 | | | | | | | | | | | | |
| 23. *Lactobacillus rhamnosus* BCRC 14029 | | | | | | | | | | | | |
| 24. *Lactobacillus rhamnosus* BCRC 80663 | | | | | | | | | | | | |
| 25. *Lactobacillus rhamnosus* BCRC 80666 | | | | | | | | | | | | |

| | mutL gene sequence identities (%) | | | | | | | | | | | |
|---|---|---|---|---|---|---|---|---|---|---|---|---|
| | 14 | 15 | 16 | 17 | 18 | 19 | 20 | 21 | 22 | 23 | 24 | 25 |
| 1. *Lactobacillus casei* BCRC 10697[T] | 78.8 | 78.8 | 78.7 | 79.3 | 78.8 | 81.2 | 81 | 81.2 | 81 | 81.5 | 80.9 | 80.9 |
| 2. *Lactobacillus casei* BCRC 17487 | 78.8 | 78.8 | 78.7 | 79.3 | 78.8 | 81.2 | 81 | 81.2 | 81 | 81.5 | 80.9 | 80.9 |
| 3. *Lactobacillus casei* BCRC 17942[T] | 78.7 | 78.7 | 78.6 | 79.1 | 78.7 | 81 | 80.9 | 81 | 80.9 | 81.3 | 80.8 | 80.8 |
| 4. *Lactobacillus casei* BCRC 80156 | 78.8 | 78.8 | 78.7 | 79.3 | 78.8 | 81.2 | 81 | 81.2 | 81 | 81.5 | 80.9 | 80.9 |
| 5. *Lactobacillus paracasei* BCRC 12248[T] | 99.3 | 99.5 | 99.9 | 99.5 | 99.7 | 77.9 | 78.7 | 78.7 | 78.7 | 78.7 | 78.8 | 78.2 |
| 6. *Lactobacillus paracasei* BCRC 12193 | 98.8 | 98.6 | 98.8 | 98.9 | 99.2 | 77.6 | 78.6 | 78.4 | 78.4 | 78.3 | 78.3 | 78 |
| 7. *Lactobacillus paracasei* BCRC 17482 | 98.9 | 99 | 99.2 | 99.3 | 99.6 | 77.6 | 78.6 | 78.4 | 78.4 | 78.3 | 78.3 | 78 |
| 8. *Lactobacillus paracasei* BCRC 16100 | 99 | 99.2 | 99.3 | 99.5 | 99.7 | 77.7 | 78.7 | 78.6 | 78.6 | 78.7 | 78.7 | 77.9 |
| 9. *Lactobacillus paracasei* BCRC 17005 | 99.5 | 99.6 | 99.7 | 99.6 | 99.9 | 77.9 | 78.8 | 78.7 | 78.7 | 78.8 | 78.8 | 78.3 |
| 10. *Lactobacillus paracasei* BCRC 18853 | 99 | 99.2 | 99.3 | 99.5 | 99.7 | 77.5 | 78.4 | 78.3 | 78.3 | 78.4 | 78.4 | 77.9 |
| 11. *Lactobacillus paracasei* BCRC 18854 | 99.2 | 99.3 | 99.5 | 99.3 | 99.9 | 77.9 | 78.8 | 78.7 | 78.7 | 78.8 | 78.8 | 78.3 |
| 12. *Lactobacillus paracasei* BCRC 17484 | 99.5 | 99.6 | 99.5 | 99.6 | 99.6 | 78 | 79 | 78.8 | 78.8 | 79 | 79 | 78.4 |
| 13. *Lactobacillus paracasei* BCRC 17488 | 99 | 99.2 | 99.3 | 99.5 | 99.7 | 77.7 | 78.7 | 78.6 | 78.6 | 78.4 | 78.4 | 78.2 |
| 14. *Lactobacillus paracasei* BCRC 17489 | | 99.3 | 99.2 | 99 | 99.3 | 78 | 79 | 78.8 | 78.8 | 79 | 79 | 78.4 |
| 15. *Lactobacillus paracasei* BCRC 14023 | | | 99.3 | 99.2 | 99.5 | 77.7 | 78.7 | 78.6 | 78.6 | 78.7 | 78.7 | 78.2 |
| 16. *Lactobacillus paracasei* BCRC 16094 | | | | 99.3 | 99.6 | 77.7 | 78.6 | 78.6 | 78.6 | 78.6 | 78.7 | 78 |
| 17. *Lactobacillus paracasei* BCRC 17002 | | | | | 99.5 | 77.9 | 78.8 | 78.7 | 78.7 | 78.8 | 78.8 | 78.3 |
| 18. *Lactobacillus paracasei* BCRC 17475 | | | | | | 77.7 | 78.7 | 78.6 | 78.6 | 78.7 | 78.7 | 78.2 |
| 19. *Lactobacillus rhamnosus* BCRC 10940[T] | | | | | | | 97.1 | 98.2 | 97.3 | 96.3 | 96.7 | 98.8 |
| 20. *Lactobacillus rhamnosus* BCRC 16000 | | | | | | | | 98.4 | 97.7 | 97.1 | 96.6 | 97.5 |
| 21. *Lactobacillus rhamnosus* BCRC 16095 | | | | | | | | | 97.4 | 96 | 97.4 | 97.3 |
| 22. *Lactobacillus rhamnosus* BCRC 17490 | | | | | | | | | | 97.5 | 96.3 | 97.1 |

TABLE 2-continued

| | | |
|---|---|---|
| 23. *Lactobacillus rhamnosus* BCRC 14029 | 97.7 | 96.7 |
| 24. *Lactobacillus rhamnosus* BCRC 80663 | | 96 |
| 25. *Lactobacillus rhamnosus* BCRC 80666 | | |

Figure 1:
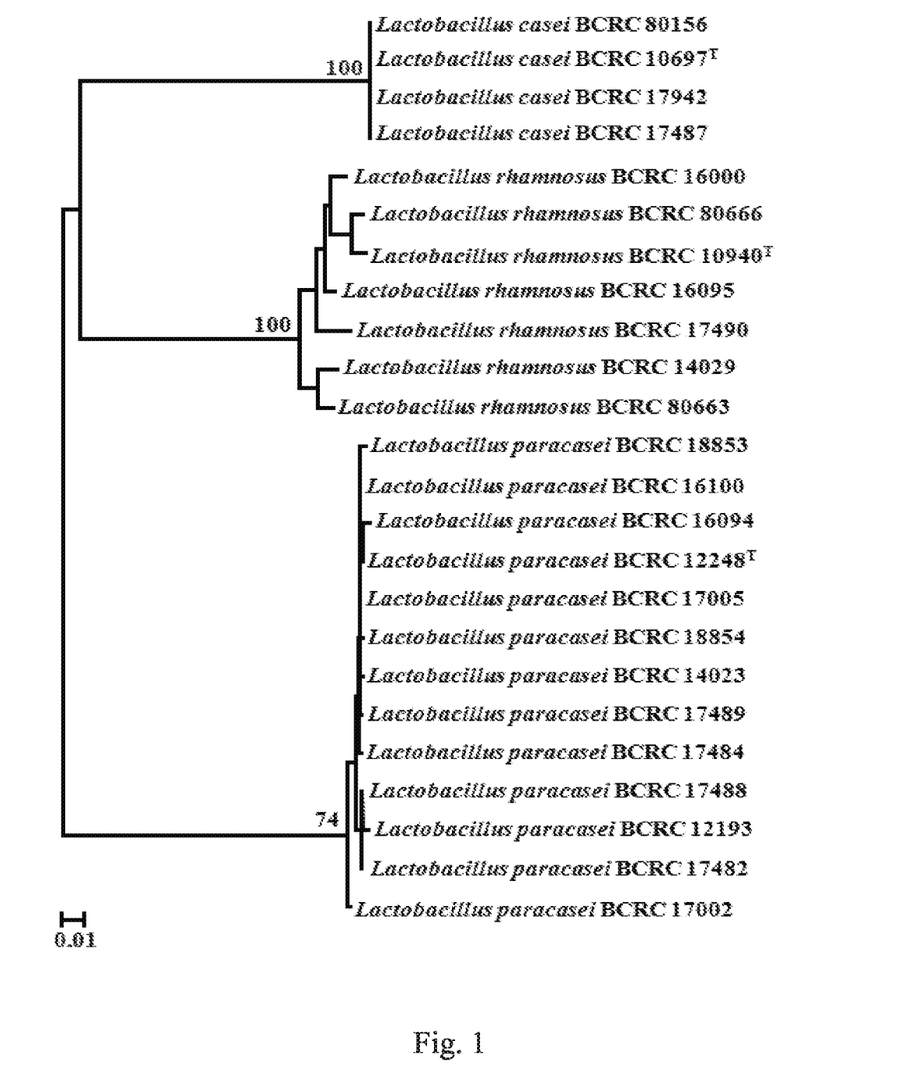
FIG. 1 shows the phylogenetic tree constructed from the sequencing results of the partial fragments of the nucleotide sequences of the mutL gene of the different related species of *Lb. casei* group.

It can be found from the results of Table 2 and FIG. 1 that the identities/similarities of the amplified sequences of mutL genes of the bacteria of *Lb. casei* group can be used to determine the interspecies of the bacteria. For example, when comparing the amplified sequence of mutL gene of a tested lactic acid bacterium with the corresponding sequences of mutL genes of the type strains of *Lb. casei*, *Lb. paracasei* and *Lb. rhamnosus*, the tested bacterium can be discriminated to the same species of the type strain to which the tested bacterium has the highest identity/similarity.

4. Intraspecific Relationship Analysis

DnaSP v.5.0 software (Librado and Rozas, 2009) was used in haplotype analysis. The results show that the tested strains *Lb. paracasei* BCRC 12248$^T$, BCRC 12193, BCRC 17482, BCRC 16100, BCRC 17005, BCRC 18853, BCRC 18854, BCRC17484, BCRC 17488, BCRC 17489, BCRC 14023, BCRC 16094, BCRC 17002, and BCRC 17457 were identified to 14 different haplotypes; and that the tested strains *Lb. rhamnosus* BCRC 10940$^T$, BCRC 80666, BCRC 16095, BCRC 17490, BCRC 16000, BCRC 80663 and BCRC 14029 were identified to 7 different haplotypes. Therefore, the amplified sequences of mutL genes of the lactic acid bacteria can be used to determine the intraspecies of the strains of *Lb. paracasei* and *Lb. rhamnosus*. For example, the amplified sequence of mutL gene of a tested bacterium, which has been identified as *Lb. paracasei* or *Lb. rhamnosus*, can be compared with each of the corresponding sequences of mutL genes of different strains of *Lb. paracasei* or *Lb. rhamnosus* to determine whether they are of the same haplotype or not.

Example 2. Determination of dnaJ Gene

1. Design of Degenerate Primers

The sequences of dnaJ genes of *Lb. casei* (AP012544; originally named *Lactobacillus casei* subsp. *casei* ATCC 393), *Lb. paracasei* (AP012541; originally named *Lactobacillus paracasei* subsp. *paracasei* JCM 8130) and *Lb. rhamnosus* ATCC 8530 (CP003094) were downloaded from GenBank. The degenerate primers, LcasDnaJ-F1 5'-TCT-GAAYTTVGTYTGRCTTTG-3' (SEQ ID NO: 3) and Lcas-DnaJ-R1 5'-GTGGTGCVCARGCKAATC-3' (SEQ ID NO: 4), wherein Y is C or T; V is G, A or C; R is A or G; and K is G or T, were designed based on the most conserved region of dnaJ gene.

2. PCR Amplification of dnaJ Gene and Nucleotide Sequencing

The partial fragments (about 620 bp) of dnaJ genes of *Lb. casei*, *Lb. paracasei* and *Lb. rhamnosus* were amplified by PCR using the above degenerate primers. PCR reaction conditions were: 30 cycles of 94° C. for 5 min, 94° C. for 1 min, 60° C. for 1 min, and 72° C. for 5 min, and a final extension step at 72° C. for 7 min. The resulting amplicons were purified by using the QIAquick PCR Purification Kit (Qiagen, U.S.A.), and then sequenced with the BigDye Terminator v3.1 Cycle Sequencing Kit (Applied Biosystems, CA, USA) and PRISM 3730 Sequencer (Applied Biosystems).

3. Interspecific Relationship Analysis

The DNA sequences of all strains were aligned by the Clustal X (1.83) program (Thompson et al., 1997), and the similarities among the sequences were calculated by the MatGAT 2.02 software (Campanella et al., 2003). Table 3 shows the similarities of all the amplified partial fragments of dnaJ genes of the tested *Lb. casei*, *Lb. paracasei* and *Lb. rhamnosus*. Neighbor-joining method (Saitou and Nei, 1987) was used to construct the phylogenetic trees of the lactic acid bacteria. As shown in the phylogenetic trees of FIG. 2, different species are distributed in different clusters.

TABLE 3

| | dnaJ gene sequence similarities (%) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 1. *Lactobacillus casei* BCRC 10697$^T$ | 100 | 100 | 99.3 | 83.2 | 82.7 | 82.9 | 82.4 | 82.7 | 83 | 83.2 | 83 | 83.6 | 82.2 | 82.7 | |
| 2. *Lactobacillus casei* BCRC 17487 | | 100 | 99.3 | 83.2 | 82.7 | 82.9 | 82.4 | 82.7 | 83 | 83.2 | 83 | 83.6 | 82.2 | 82.7 | |
| 3. *Lactobacillus casei* BCRC 80156 | | | 99.3 | 83.2 | 82.7 | 82.9 | 82.4 | 82.7 | 83 | 83.2 | 83 | 83.6 | 82.2 | 82.7 | |
| 4. *Lactobacillus casei* BCRC 17647 | | | | 83.6 | 83 | 83.2 | 82.7 | 83 | 83.4 | 83.6 | 83.4 | 83.9 | 82.5 | 83 | |
| 5. *Lactobacillus paracasei* BCRC 12248$^T$ | | | | | 97.4 | 97.9 | 97.1 | 98.3 | 97.6 | 97.1 | 96.7 | 97.9 | 97.1 | 98.3 | |
| 6. *Lactobacillus paracasei* BCRC 12188 | | | | | | 98.1 | 98.6 | 98.1 | 98.4 | 96.5 | 96.5 | 97.1 | 99.3 | 98.1 | |
| 7. *Lactobacillus paracasei* BCRC 14001 | | | | | | | 97.4 | 98.3 | 97.9 | 97.1 | 97.8 | 97.2 | 98.1 | 98.3 | |
| 8. *Lactobacillus paracasei* BCRC 16100 | | | | | | | | 98.1 | 98.4 | 96.9 | 96.9 | 96.7 | 98.6 | 98.1 | |
| 9. *Lactobacillus paracasei* BCRC 17001 | | | | | | | | | 98.3 | 97.1 | 97.1 | 97.9 | 98.1 | 99.3 | |
| 10. *Lactobacillus paracasei* BCRC 17005 | | | | | | | | | | 96.7 | 96.4 | 97.2 | 98.1 | 98.3 | |
| 11. *Lactobacillus paracasei* BCRC 17475 | | | | | | | | | | | 99.3 | 98.1 | 96.2 | 97.1 | |
| 12. *Lactobacillus paracasei* BCRC 17483 | | | | | | | | | | | | 97.8 | 96.5 | 97.1 | |
| 13. *Lactobacillus paracasei* BCRC 17484 | | | | | | | | | | | | | 96.7 | 97.9 | |
| 14. *Lactobacillus paracasei* BCRC 17488 | | | | | | | | | | | | | | 98.4 | |
| 15. *Lactobacillus paracasei* BCRC 17489 | | | | | | | | | | | | | | | |
| 16. *Lactobacillus paracasei* BCRC 14023 | | | | | | | | | | | | | | | |
| 17. *Lactobacillus paracasei* BCRC 12193 | | | | | | | | | | | | | | | |
| 18. *Lactobacillus paracasei* BCRC 14073 | | | | | | | | | | | | | | | |
| 19. *Lactobacillus paracasei* BCRC 16094 | | | | | | | | | | | | | | | |
| 20. *Lactobacillus paracasei* isolate 275 | | | | | | | | | | | | | | | |
| 21. *Lactobacillus rhamnosus* BCRC 10940$^T$ | | | | | | | | | | | | | | | |
| 22. *Lactobacillus rhamnosus* BCRC 14029 | | | | | | | | | | | | | | | |

TABLE 3-continued

23. *Lactobacillus rhamnosus* BCRC 16000
24. *Lactobacillus rhamnosus* BCRC 16095
25. *Lactobacillus rhamnosus* BCRC 17004
26. *Lactobacillus rhamnosus* BCRC 17490
27. *Lactobacillus rhamnosus* BCRC 80666
28. *Lactobacillus rhamnosus* BCRC 17007
29. *Lactobacillus rhamnosus* BCRC 11197
30. *Lactobacillus rhamnosus* BCRC 11673

| | dnaJ gene sequence similarities (%) | | | | | | | | | | | | | | |
|---|---|---|---|---|---|---|---|---|---|---|---|---|---|---|---|
| | 16 | 17 | 18 | 19 | 20 | 21 | 22 | 23 | 24 | 25 | 26 | 27 | 28 | 29 | 30 |
| 1. *Lactobacillus casei* BCRC 10697[T] | 83.2 | 82.2 | 83.2 | 83.2 | 82.7 | 85.5 | 84.6 | 85.1 | 84.9 | 84.8 | 85.1 | 84.1 | 85.5 | 85.5 | 85.5 |
| 2. *Lactobacillus casei* BCRC 17487 | 83.2 | 82.2 | 83.2 | 83.2 | 82.7 | 85.5 | 84.6 | 85.1 | 84.9 | 84.8 | 85.1 | 84.1 | 85.5 | 85.5 | 85.5 |
| 3. *Lactobacillus casei* BCRC 80156 | 83.2 | 82.2 | 83.2 | 83.2 | 82.7 | 85.5 | 84.6 | 85.1 | 84.9 | 84.8 | 85.1 | 84.1 | 85.5 | 85.5 | 85.5 |
| 4. *Lactobacillus casei* BCRC 17647 | 83.6 | 82.5 | 83.6 | 83.6 | 83 | 85.3 | 84.4 | 84.9 | 84.8 | 84.6 | 84.9 | 83.9 | 85.3 | 85.3 | 85.3 |
| 5. *Lactobacillus paracasei* BCRC 12248[T] | 100 | 97.1 | 100 | 100 | 97.9 | 81.7 | 81.8 | 82.2 | 82.4 | 82 | 82.2 | 82 | 81.7 | 81.7 | 81.7 |
| 6. *Lactobacillus paracasei* BCRC 12188 | 97.4 | 99.3 | 97.4 | 97.4 | 97.8 | 81.8 | 82.4 | 82.4 | 82.5 | 82.5 | 82.4 | 82.5 | 81.8 | 81.8 | 81.8 |
| 7. *Lactobacillus paracasei* BCRC 14001 | 97.9 | 98.1 | 97.9 | 97.9 | 98.6 | 82.2 | 82.4 | 82.7 | 82.9 | 82.5 | 82.7 | 82.5 | 82.2 | 82.2 | 82.2 |
| 8. *Lactobacillus paracasei* BCRC 16100 | 97.1 | 98.6 | 97.1 | 97.1 | 97.1 | 80.6 | 81.1 | 81.1 | 81.3 | 81.3 | 81.5 | 81.3 | 80.6 | 80.6 | 80.6 |
| 9. *Lactobacillus paracasei* BCRC 17001 | 98.3 | 98.1 | 98.3 | 98.3 | 97.9 | 81.8 | 82 | 82.4 | 82.5 | 82.2 | 82.4 | 82.2 | 81.8 | 81.8 | 81.8 |
| 10. *Lactobacillus paracasei* BCRC 17005 | 97.6 | 98.1 | 97.6 | 97.6 | 97.2 | 81.3 | 81.8 | 81.8 | 82 | 82 | 81.8 | 82 | 81.3 | 81.3 | 81.3 |
| 11. *Lactobacillus paracasei* BCRC 17475 | 97.1 | 96.2 | 97.1 | 97.1 | 97.4 | 82.2 | 81.7 | 82.7 | 82.9 | 81.8 | 83 | 82.2 | 82.2 | 82.2 | 82.2 |
| 12. *Lactobacillus paracasei* BCRC 17483 | 96.7 | 96.5 | 96.7 | 96.7 | 97.8 | 82.4 | 81.8 | 82.9 | 83 | 82 | 83.2 | 82.4 | 82.4 | 82.4 | 82.4 |
| 13. *Lactobacillus paracasei* BCRC 17484 | 97.9 | 96.7 | 97.9 | 97.9 | 97.6 | 82.7 | 82.2 | 83.2 | 83.7 | 82.4 | 83.2 | 82.7 | 82.7 | 82.7 | 82.7 |
| 14. *Lactobacillus paracasei* BCRC 17488 | 97.1 | 100 | 97.1 | 97.1 | 97.8 | 81.5 | 82 | 82 | 82.2 | 82.2 | 82 | 82.2 | 81.5 | 81.5 | 81.5 |
| 15. *Lactobacillus paracasei* BCRC 17489 | 98.3 | 98.4 | 98.3 | 98.3 | 97.9 | 81.5 | 81.7 | 82 | 82.2 | 81.8 | 82 | 81.8 | 81.5 | 81.5 | 81.5 |
| 16. *Lactobacillus paracasei* BCRC 14023 | | 97.1 | 100 | 100 | 97.9 | 81.7 | 81.8 | 82.2 | 82.4 | 82 | 82.2 | 82 | 81.7 | 81.7 | 81.7 |
| 17. *Lactobacillus paracasei* BCRC 12193 | | | 97.1 | 97.1 | 97.8 | 81.5 | 82 | 82 | 82.2 | 82.2 | 82 | 82.2 | 81.5 | 81.5 | 81.5 |
| 18. *Lactobacillus paracasei* BCRC 14073 | | | | 100 | 97.9 | 81.7 | 81.8 | 82.2 | 82.4 | 82 | 82.2 | 82 | 81.7 | 81.7 | 81.7 |
| 19. *Lactobacillus paracasei* BCRC 16094 | | | | | 97.9 | 81.7 | 81.8 | 82.2 | 82.4 | 82 | 82.2 | 82 | 81.7 | 81.7 | 81.7 |
| 20. *Lactobacillus paracasei* isolate 275 | | | | | | 82.5 | 82.7 | 83 | 83.2 | 82.9 | 83 | 82.9 | 82.5 | 82.5 | 82.5 |
| 21. *Lactobacillus rhamnosus* BCRC 10940[T] | | | | | | | 98.8 | 98.4 | 98.1 | 99 | 98.3 | 98.1 | 100 | 100 | 100 |
| 22. *Lactobacillus rhamnosus* BCRC 14029 | | | | | | | | 97.6 | 97.2 | 99.8 | 97.4 | 98.6 | 98.8 | 98.8 | 98.8 |
| 23. *Lactobacillus rhamnosus* BCRC 16000 | | | | | | | | | 99 | 97.8 | 99.1 | 97.9 | 98.4 | 98.4 | 98.4 |
| 24. *Lactobacillus rhamnosus* BCRC 16095 | | | | | | | | | | 97.4 | 98.8 | 97.9 | 98.1 | 98.1 | 98.1 |
| 25. *Lactobacillus rhamnosus* BCRC 17004 | | | | | | | | | | | 97.6 | 98.8 | 99 | 99 | 99 |
| 26. *Lactobacillus rhamnosus* BCRC 17490 | | | | | | | | | | | | 97.8 | 98.3 | 98.3 | 98.3 |
| 27. *Lactobacillus rhamnosus* BCRC 80666 | | | | | | | | | | | | | 98.1 | 98.1 | 98.1 |
| 28. *Lactobacillus rhamnosus* BCRC 17007 | | | | | | | | | | | | | | 100 | 100 |
| 29. *Lactobacillus rhamnosus* BCRC 11197 | | | | | | | | | | | | | | | 100 |
| 30. *Lactobacillus rhamnosus* BCRC 11673 | | | | | | | | | | | | | | | |

Figure 2:
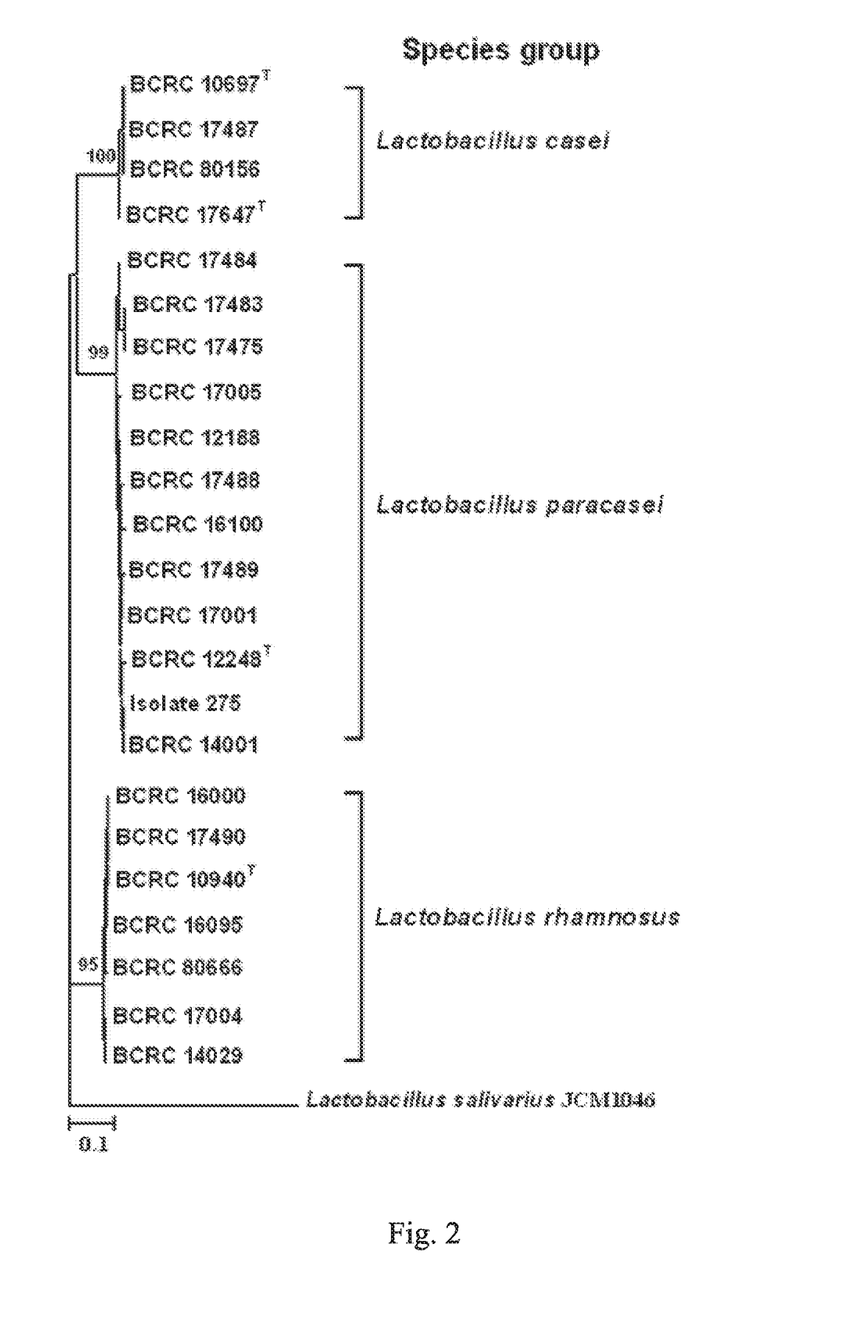
FIG. 2 shows the phylogenetic tree constructed from the sequencing results of the partial fragments of the nucleotide sequences of the dnaJ gene of the different related species of *Lb. casei* group.

It can be found from the results of Table 3 and FIG. 2 that the identities/similarities of the amplified sequences of dnaJ genes of the bacteria of *Lb. casei* group can be used to determine the interspecies of the bacteria. For example, when comparing the amplified sequence of dnaJ gene of a tested lactic acid bacterium with the corresponding sequences of dnaJ genes of the type strains of *Lb. casei*, *Lb. paracasei* and *Lb. rhamnosus*, the tested bacterium can be discriminated to the same species of the type strain to which the tested bacterium has the highest identity/similarity.

4. Intraspecific Relationship Analysis

DnaSP v.5.0 software (Librado and Rozas, 2009) was used in haplotype analysis. The results show that the tested strains *Lb. paracasei* BCRC 12248[T], BCRC 12188, BCRC 14001, BCRC 16100, BCRC 17001, BCRC 17005, BCRC 17475, BCRC 17483, BCRC 17484, BCRC 17488, BCRC 17489 and isolated strain 275 were identified to 12 different haplotypes; and that the tested strains *Lb. rhamnosus* BCRC 10940^T, BCRC 14029, BCRC 16000, BCRC 16095, BCRC 17004, BCRC 17490, and BCRC 80666 were identified to 7 different haplotypes. Therefore, the amplified sequences of 5 dnaJ genes of the lactic acid bacteria can be used to determine the intraspecies of the strains of *Lb. paracasei* and *Lb. rhamnosus*. For example, the amplified sequence of dnaJ gene of a tested bacterium, which has been identified as *Lb. paracasei* or *Lb. rhamnosus*, can be compared with each of the corresponding sequences of mutL genes of different strains of *Lb. paracasei* or *Lb. rhamnosus* to determine whether they are of the same haplotype or not.

a second primer mixture comprising the nucleotide sequences shown as 5'-GTGGTGCVCARGCKAATC-3' (SEQ ID NO: 4), wherein V=G, A or C; R=A or G; and K=G or T.

2. A composition comprising the first primer mixture and/or the second primer mixture of claim 1, and a solvent.

3. A method for determining the species of a lactic acid bacterium of *Lactobacillus casei* group, which comprises:
 (a) extracting a DNA sample from the lactic acid bacterium;
 (b) using the primer pair of claim 1 to amplify the DNA sample to obtain a partial fragment of the nucleotide

---

---

What is claimed is:

1. A degenerate primer pair comprising:
 a first primer mixture comprising the nucleotide sequences shown as 5'-ATTGAYCARCTATCKGC-MAC-3' (SEQ ID NO: 1), wherein Y=C or T; R=A or G; K=G or T; and M=A or C, and
 a second primer mixture comprising the nucleotide sequences shown as 5'-GAGCCRTAACCG-GCAATMA-3' (SEQ ID NO: 2), wherein R=A or G; and M=A or C; or
 a first primer mixture comprising the nucleotide sequences shown as 5'-TCTGAAYTTVGTYT-GRCTTTG-3' (SEQ ID NO: 3), wherein Y=C or T; V=G, A or C; and R=A or G, and sequence of mutL gene and/or a partial fragment of the nucleotide sequence of dnaJ gene;
 (c) determining the sequence of the amplified partial fragment; and
 (d) comparing the determined sequence with the corresponding gene sequences of two or more type strains of *Lb. casei* group to obtain a percent similarity and/or identity to each of the type strains, thereby identifying the lactic acid bacterium as the same species as the type strain of *Lb. casei* group to which the lactic acid bacterium has the highest percent similarity and/or identity.

4. The method of claim 3, wherein step (b) uses a first primer mixture comprising the nucleotide sequences shown as 5'-ATTGAYCARCTATCKGCMAC-3' (SEQ ID NO: 1), wherein Y=C or T; R=A or G; K=G or T; and M=A or C, and a second primer mixture comprising the nucleotide sequences shown as 5'-GAGCCRTAACCGGCAATMA-3' (SEQ ID NO: 2), wherein R=A or G; and M=A or C, to amplify the DNA sample to obtain the partial fragment of the nucleotide sequence of mutL gene.

5. The method of claim 3, wherein step (b) uses a first primer mixture comprising the nucleotide sequences shown as 5'-TCTGAAYTTVGTYTGRCTTTG-3' (SEQ ID NO: 3), wherein Y=C or T; V=G, A or C; and R=A or G, and a second primer mixture comprising the nucleotide sequences shown as 5'-GTGGTGCVCARGCKAATC-3' (SEQ ID NO: 4), wherein V=G, A or C; R=A or G; and K=G or T, to amplify the DNA sample to obtain the partial fragment of the nucleotide sequence of dnaJ gene.

6. The method of claim 3, wherein the two or more type strains of *Lb. casei* group are *Lb. casei* BCRC 10697$^T$ (ATCC 393), *Lb. paracasei* BCRC 12248$^T$ (ATCC 25302), and *Lb. rhamnosus* BCRC 10940$^T$ (ATCC 12116), or any combinations thereof.

7. A method for determining whether a lactic acid bacterium of *Lb. casei* group and two or more other lactic acid bacteria of *Lb. casei* group that are of the same species but different strains are of the same haplotype or not, which comprises:
   (a) extracting a DNA sample from the lactic acid bacterium;
   (b) using the primer pair of claim 1 to amplify the DNA sample to obtain a partial fragment of the nucleotide sequence of mutL gene and/or a partial fragment of the nucleotide sequence of dnaJ gene;
   (c) determining the sequence of the amplified partial fragment; and
   (d) conducting haplotype analysis to compare the determined sequence with each corresponding gene sequence of the two or more other lactic acid bacteria of the same species but different strains, wherein if the analyzed sequences are different from each other, it represents that the compared lactic acid bacteria are of different haplotypes.

8. The method of claim 7, wherein step (b) uses a first primer mixture comprising the nucleotide sequences shown as 5'-ATTGAYCARCTATCKGCMAC-3' (SEQ ID NO: 1), wherein Y=C or T; R=A or G; K=G or T; and M=A or C, and a second primer mixture comprising the nucleotide sequences shown as 5'-GAGCCRTAACCGGCAATMA-3' (SEQ ID NO: 2), wherein R=A or G; and M=A or C, to amplify the DNA sample to obtain the partial fragment of the nucleotide sequence of mutL gene.

9. The method of claim 7, wherein step (b) uses a first primer mixture comprising the nucleotide sequences shown as 5'-TCTGAAYTTVGTYTGRCTTTG-3' (SEQ ID NO: 3), wherein Y=C or T; V=G, A or C; and R=A or G, and a second primer mixture comprising the nucleotide sequences shown as 5'-GTGGTGCVCARGCKAATC-3' (SEQ ID NO: 4), wherein V=G, A or C; R=A or G; and K=G or T, to amplify the DNA sample to obtain the partial fragment of the nucleotide sequence of dnaJ gene.

10. The method of claim 7, wherein the two or more lactic acid bacteria of *Lb. casei* group of the same species are different strains of *Lb. paracasei*.

11. The method of claim 10, wherein the strain of *Lb. paracasei* is selected from *Lb. paracasei* BCRC 12248$^T$, *Lb. paracasei* BCRC 12188, *Lb. paracasei* BCRC 14001, *Lb. paracasei* BCRC 16100, *Lb. paracasei* BCRC 17001, *Lb. paracasei* BCRC 17005, *Lb. paracasei* BCRC 17475, *Lb. paracasei* BCRC 17483, *Lb. paracasei* BCRC 17484, *Lb. paracasei* BCRC 17488, *Lb. paracasei* BCRC 17489, *Lb. paracasei* BCRC 12193, *Lb. paracasei* BCRC 18853, *Lb. paracasei* BCRC 18854, *Lb. paracasei* BCRC 14023, *Lb. paracasei* BCRC 16094, and *Lb. paracasei* BCRC 17002.

12. The method of claim 7, wherein the two or more lactic acid bacteria of *Lb. casei* group of the same species are different strains of *Lb. rhamnosus*.

13. The method of claim 12, wherein the strain of *Lb. rhamnosus* is selected from *Lb. rhamnosus* BCRC 10940$^T$, *Lb. rhamnosus* BCRC 14029, *Lb. rhamnosus* BCRC 16000, *Lb. rhamnosus* BCRC 16095, *Lb. rhamnosus* BCRC 17004, *Lb. rhamnosus* BCRC 17490, *Lb. rhamnosus* BCRC 80663, and *Lb. rhamnosus* BCRC 80666.

14. A kit comprising the primer pair of claim 1.

15. The kit of claim 14, which further comprises a computer readable medium comprising the sequence information of mutL gene and/or dnaJ gene of at least one lactic acid bacterium of *Lb. casei* group.

16. The kit of claim 14, wherein the at least one lactic acid bacterium of *Lb. casei* group is selected from *Lb. casei* BCRC 10697$^T$, *Lb. casei* BCRC 17487, *Lb. casei* BCRC 17942, *Lb. casei* BCRC 80156, *Lb. casei* BCRC 17647, *Lb. paracasei* BCRC 12248$^T$, *Lb. paracasei* BCRC 12188, *Lb. paracasei* BCRC 14001, *Lb. paracasei* BCRC 16100, *Lb. paracasei* BCRC 17001, *Lb. paracasei* BCRC 17005, *Lb. paracasei* BCRC 17475, *Lb. paracasei* BCRC 17483, *Lb. paracasei* BCRC 17484, *Lb. paracasei* BCRC 17488, *Lb. paracasei* BCRC 17489, *Lb. paracasei* BCRC 12193, *Lb. paracasei* BCRC 18853, *Lb. paracasei* BCRC 18854, *Lb. paracasei* BCRC 14023, *Lb. paracasei* BCRC 16094, *Lb. rhamnosus* BCRC 10940T, *Lb. rhamnosus* BCRC 14029, *Lb. rhamnosus* BCRC 16000, *Lb. rhamnosus* BCRC 16095, *Lb. rhamnosus* BCRC 17004, *Lb. rhamnosus* BCRC 17490, *Lb. rhamnosus* BCRC 80663, *Lb. rhamnosus* BCRC 80666, and any combinations thereof.

* * * * *